(12) United States Patent
Khouri et al.

(10) Patent No.: US 6,235,866 B1
(45) Date of Patent: May 22, 2001

(54) SLURRY PREPARATION OF BIS (HALOPHTHALIMIDES) AND OF POLYETHER POLYMERS

(75) Inventors: Farid Fouad Khouri; Ganesh Kailasam, both of Clifton Park; Joseph John Caringi, Niskayuna; Peter David Phelps, Schenectady; Paul Edward Howson, Latham, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/413,376

(22) Filed: Oct. 6, 1999

(51) Int. Cl.$^7$ .............................. C08G 8/02; C08G 69/26; C08G 73/10; C08G 75/00

(52) U.S. Cl. ........................ 528/125; 528/26; 528/126; 528/128; 528/170; 528/171; 528/172; 528/173; 528/174; 528/176; 528/179; 528/182; 528/185; 528/188; 528/220; 528/229; 528/353; 525/425; 525/436; 525/439

(58) Field of Search ..................... 528/125, 126, 528/128, 170, 171, 353, 172, 173, 176, 174, 175, 182, 185, 188, 220, 229, 26, 17; 525/425, 439, 436

(56) References Cited

U.S. PATENT DOCUMENTS

| | | |
|---|---|---|
| 3,787,364 | 1/1974 | Wirth et al. .................... 528/170 |
| 4,257,953 | 3/1981 | Williams ......................... 568/723 |
| 4,273,712 | 6/1981 | Williams ......................... 568/723 |
| 5,229,482 | 7/1993 | Brunelle ......................... 528/170 |
| 5,830,974 | 11/1998 | Schmidhauser et al. ........... 528/170 |
| 5,908,915 | * 6/1999 | Brunelle ......................... 528/170 |
| 6,001,957 | * 12/1999 | Puyenbroek et al. ............. 528/170 |
| 6,011,122 | * 1/2000 | Puyenbroek .................... 525/425 |
| 6,020,456 | * 2/2000 | Brunelle et al. ................. 528/353 |

\* cited by examiner

*Primary Examiner*—P. Hampton-Hightower
(74) *Attorney, Agent, or Firm*—S. Bruce Brown; Noreen C. Johnson

(57) ABSTRACT

Bis(halophthalimides) such as, 3-bis[N-(4-chlorophthalimido)]benzene are prepared in slurry in an organic liquid such as o-dichlorobenzene or anisole, by a reaction at a temperature of at least 150° C. between at least one diamino compound, preferably an aromatic diamine such as m- or p-phenylenediamine, and at least one halophthalic anhydride such as 4-chlorophthalic anhydride, in the presence of an imidization catalyst such as sodium phenylphosphinate. The solids content of the reaction mixture is at least about 5% and preferably at least about 12% by weight. The product slurry may be employed directly in the preparation of polyetherimides, and similar slurries may be employed to prepare other polyether polymers.

35 Claims, No Drawings

SLURRY PREPARATION OF BIS (HALOPHTHALIMIDES) AND OF POLYETHER POLYMERS

BACKGROUND OF THE INVENTION

This invention relates to the preparation of polyether polymers and intermediates therefor. More particularly, it relates to the preparation of bis(halophthalimides), their isolation as a slurry and their use in slurry form for the preparation of polyetherimides.

Various types of aromatic polyethers, particularly polyetherimides but also including polyethersulfones, polyetherketones, and polyetheretherketones, have become important as engineering resins by reason of their excellent properties. These polymers are typically prepared by the reaction of salts of dihydroxyaromatic compounds, such as bisphenol A disodium salt, with dihaloaromatic molecules. For example, polyetherimides are conveniently prepared by the reaction of salts of dihydroxyaromatic compounds with bis(halophthalimides) as illustrated by 1,3-bis[N-(4-chlorophthalimido)]benzene (hereinafter sometimes "ClPAMI"), which has the structure

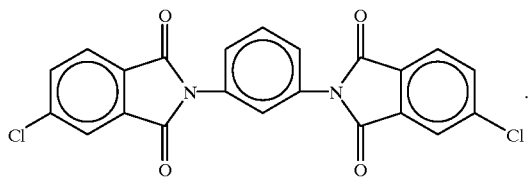

For polysulfones and polyetherketones, bis(4-fluorophenyl) sulfone, bis(4-chlorophenyl) sulfone and the analogous ketones are typically employed.

According to U.S. Pat. Nos. 5,229,482 and 5,830,974, the preparation of aromatic polyethers may be conducted in solution in relatively non-polar solvents, using a phase transfer catalyst which is substantially stable under the temperature conditions employed. Solvents disclosed in U.S. Pat. No. 5,229,482 include o-dichlorobenzene, dichlorotoluene, 1,2,4-trichlorobenzene and diphenyl sulfone. In U.S. Pat. No. 5,830,974, monoalkoxybenzenes such as anisole, diphenylether, or phenetole are employed. Solvents of the same types may be used for the preparation of bis(halophthalimide) intermediates for polyetherimides.

Each of these patents requires introduction into the reaction mixture of the bis(halophthalimide) as a substantially pure, isolated compound. This is often difficult, since solid bis(halophthalimides) are typically of very low density and fluffy, making weighing and handling burdensome. It would be desirable, for both technical and cost reasons, to handle such reactants as slurries in an organic solvent instead of in dry solid form.

In order to isolate bis(halophthalimides) in slurry form, however, it is often preferred to prepare them by a method which employs the reactants, namely diamino compound and halophthalic anhydride, in equimolar proportions so as to avoid competing reactions. According to such prior art as U.S. Pat. No. 3,787,364, the employment of substantially equimolar proportions of reactants can result in the necessity for extremely long reaction times, typically up to 3 days. This is true even when such active solvents as glacial acetic acid are employed. When non-polar solvents are employed, it has typically been necessary to employ one reactant, most often the chlorophthalic anhydride, in excess, whereupon said reactant is still present after completion of the reaction and can cause competing reactions to take place upon synthesis of the polyetherimide.

SUMMARY OF THE INVENTION

The present invention is based in part on the discovery that bis(halophthalimides) may be prepared in high yield and conversion by the reaction of halophthalic anhydride and diamino compound, even in equimolar amounts, and may be isolated in slurry rather than solid form, if certain reaction conditions are maintained. These include relatively high reaction temperatures, relatively high solids content and the presence of a suitable catalyst.

The invention in one of its aspects is a method for preparing a bis(halophthalimide) in organic slurry form which comprises effecting contact at a temperature of at least 100° C. between the constituents of a mixture comprising at least one diamino compound, at least one halophthalic anhydride, a relatively non-polar organic liquid and an imidization catalyst, said mixture having a solids content of at least about 5% by weight, thereby producing a slurry of said bis(halophthalimide) in said liquid.

It has also been discovered that bis(halophthalimides) and similar dihaloaromatic compounds may be employed in slurry form for the preparation of the corresponding polyether polymers. Another aspect of the invention, therefore, is a method for preparing an aromatic polyether polymer which comprises contacting, in at least one relatively non-polar organic liquid as diluent, substantially equimolar amounts of at least one alkali metal salt of a dihydroxy-substituted aromatic hydrocarbon and a slurry in said organic liquid of at least one substituted aromatic compound of the formula $$Z(A^1-X^1)_2, \quad (I)$$

wherein Z is an activating radical, $A^1$ is an aromatic radical and $X^1$ is fluoro, chloro, bromo or nitro, in the presence of a catalytically active amount of a phase transfer catalyst.

DETAILED DESCRIPTION PREFERRED EMBODIMENTS

Any diamino compound may be employed in the method of this invention. Examples of suitable compounds are ethylenediamine, propylenediamine, trimethylenediamine, diethylenetriamine, triethylenetetramine, heptamethylenediamine, octamethylenediamine, 1,12-dodecanediamine, 1,18-octadecanediamine, 3-methylheptamethylenediamine, 4,4'-dimethylheptamethylenediamine, 4-methylnonamethylenediamine, 2,5-dimethylhexamethylenediamine, 2,2-dimethylpropylenediamine, N-methyl-bis(3-aminopropyl) amine, 3-methoxyhexamethylenediamine, 1,2-bis(3-aminopropoxy)ethane, bis(3-aminopropyl) sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylenediamine, 5-methyl-4,6-diethyl-1,3-phenylenediamine, benzidine, 3,3'-dimethylbenzidine, 3,3'-dimethoxybenzidine, 1,5-diaminonaphthalene, bis(4-aminophenyl)methane, bis(2-chloro-4-amino-3,5-diethylphenyl)methane, bis(4-aminophenyl)propane, 2,4-bis (β-amino-t-butyl)toluene, bis(p-β-methyl-o-aminopentyl) benzene, 1,3-diamino-4-isopropylbenzene, bis(4-aminophenyl) sulfone, bis(4-aminophenyl) ether and 1,3-bis (3-aminopropyl)tetramethyldisiloxane. Mixtures of these compounds may also be present. The preferred diamino compounds are aromatic diamines, especially m- and p-phenylenediamine and mixtures thereof.

The halophthalic anhydrides may be represented by the formula

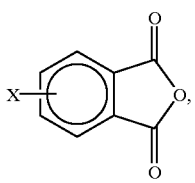

(II)

wherein X is chloro, bromo or fluoro, preferably chloro. The substituent X may be on any free valence position of the aromatic ring. Especially preferred is 4-chlorophthalic anhydride.

Also required according to the invention is a relatively non-polar organic liquid, usually having a substantially lower polarity than that of the dipolar aprotic solvents such as dimethylformamide, dimethylacetamide and N-methylpyrrolidinone. Said non-polar solvent preferably has a boiling point above about 100° C. and most preferably above about 150° C., in order to facilitate the reaction which requires temperatures above that temperature. Suitable liquids of this type include o-dichlorobenzene, dichlorotoluene, 1,2,4-trichlorobenzene, diphenyl sulfone and monoalkoxybenzenes such as anisole, and more generically liquids whose polarity is no higher than those of the aforementioned liquids. Liquids of similar polarity but lower boiling points, such as chlorobenzene, may be employed at super-atmospheric pressures. Anisole and o-dichlorobenzene are usually preferred.

In conventional methods for the production of bis (halophthalimides), as disclosed, for example, in the aforementioned U.S. Pat. No. 3,787,364, the halophthalic anhydride is present in slight excess to drive the reaction to completion. A principal advantage of the present invention, however, is the fact that such an excess is not necessary. Rather, it is possible to employ stoichiometric proportions of the reagents, or to begin with an excess of one reagent and subsequently introduce the other to the stoichiometric amount, depending on analytical data for the concentration of one or both reagents. Thus, bis(halophthalimide) may be produced in slurry form without isolation and separation from reactants and other by-products, with a high degree of conversion to the desired bis(halophthalimide). For this purpose it is required to employ an imidization catalyst to provide a sufficiently fast reaction rate. Suitable imidization catalysts are known in the art; they include salts of organo-phosphorus acids, particularly phosphinates such as sodium phenylphosphinate and heterocyclic amines such as 4-diaminopyridine. Sodium phenylphosphinate is generally preferred.

The bis(halophthalimide) preparation method of the invention typically employs temperatures of at least 110° C., preferably in the range from 150° to about 225° C., preferably about 175–225° C. At temperatures below 110° C., reaction rates are for the most part too slow for economical operation. It is within the scope of the invention to employ super-atmospheric pressures, typically up to about 5 atm, to facilitate the use of high temperatures without causing liquid to be lost by evaporation through boiling.

A further feature, for the same reason, is a solids content in the reaction mixture of at least about 5%, preferably at least about 12% and most preferably about 15–25%, by weight. By "solids content" is meant the proportion of reactants (i.e., diamine and anhydride) as a percentage of the total weight including liquids. It is further within the scope of the invention to change the solids content during the reaction, for such reasons as to effectuate transfer of the reaction mixture from one vessel to another.

Other constituent proportions in the reaction mixture preferably include, for reasons already stated, a 2:1 molar ratio of anhydride to diamine. While other ratios may be employed, there is generally no advantage in doing so. Catalyst is present in an amount effective to accelerate the reaction, usually about 0.1–0.3% by weight based on the total of diamine and anhydride.

Water removal from the system to drive conversion and drying can be accomplished on a continuous basis in either batch, semi-continuous or continuous processes using means well-known in the art such as a distillation column in conjunction with one or more reactors. In one embodiment, a mixture of water and non-polar organic liquid distilling from a reactor is sent to a distillation column where water is taken off overhead and solvent is recycled back into the reactor at a rate to maintain or increase the desired solids concentration. Other methods for water removal include, but are not limited to, passing the condensed distillate through a drying bed for chemical or physical adsorption of water.

The product of said method is a slurry containing the desired bis(halophthalimide) in combination with such by-products as structurally related amic acids, illustrated by that of the formula

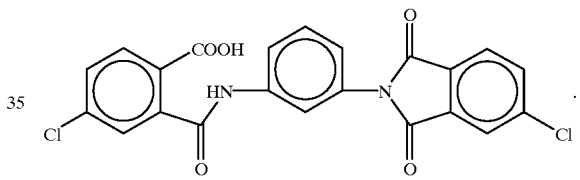

It is within the scope of the invention to further decrease the proportion of organic liquid in the slurry, reducing it to the consistency of a paste, and for the purpose of the invention such a paste is deemed to be a slurry, the only variation being in amount of liquid.

Since the yield in the imidization reaction is essentially quantitative, bis(halophthalimide) and amic acids are the only significant products of the reaction of diamino compound with halophthalic anhydride. To ensure subsequent formation of polyetherimide at an acceptable rate to a high molecular weight product, it is highly preferred for the conversion to bisimide (i.e., the proportion of bisimide as a percentage of total bisimide and related amic acids) to be at least 99.75% and the invention is capable of producing conversions at this level. If amic acids are present in amounts larger than 0.25%, they may be incorporated in the polymer in the form of their carboxylate salt resulting in decreased thermal stability of the final resin. The carboxylate salts may be generated by reaction of amic acid with bisphenol salt to form bisphenol or its monosodium salt and hence changing the reaction stoichiometry or generating a chain terminating agent, which typically results in a decrease in the polymer molecular weight.

Also, it is within the scope of the invention to employ halophthalic anhydrides containing measurable proportions of unsubstituted phthalic anhydride as an impurity. In the subsequent polyetherimide-forming reaction, it will be present in the form of a monohalo compound such as 1-[N-(4-chlorophthalimido)]-3-(N-phthalimido)benzene (hereinafter "m-ClPAMI"), which serves as a chain termination agent and which can be compensated for by adjusting the stoichiometry of the polyetherimide-forming reagents.

The bis(halophthalimide) preparation method of this invention is illustrated by the following examples. All percentages in the examples herein are by weight unless otherwise indicated.

EXAMPLES 1–3

In each example, a 250 milliliter (ml) three-necked round-bottomed flask fitted with a stirrer and Dean-Stark trap was charged with 1,980.6 milligrams (mg) (18.315 millimoles [mmol]) of m-phenylenediamine, 6,687.2 mg (36.63 mmol) of 4-chlorophthalic anhydride and 14.67 mg of sodium phenylphosphinate. Anisole was added to afford the desired solids percentage and the flask was heated for 0.5 hour with stirring in a 198° C. oil bath, a temperature effective to produce gentle refluxing without distillation. The temperature was then raised to a specified temperature and water was collected in the trap until water evolution was complete. The remaining material in the flask was the desired ClPAMI slurry in anisole. Finally, the trap was replaced with a distillation head and the anisole was stripped to leave a paste that was analyzed by high pressure liquid chromatography.

The results are given in Table I. The yield of ClPAMI and corresponding amic acids was quantitative in each example, but conversion to ClPAMI varied and is given in the table. In Example 3, after a first stage, the reaction mixture was transferred to a pressure vessel with addition of anisole and a second stage was performed at about 200° C. reaction temperature and 2.4 atmospheres pressure (atm.). Comparison was made with a control employing a lower solids proportion.

TABLE I

| Example | 1 | 2 | 3 | Control |
|---|---|---|---|---|
| Solids, % | 20 | 20 | 20/16.26 | 9.85 |
| Reaction time, hrs. | 4.5 | 7 | 2/2.5 | 40 |
| Conversion, % | 99.44 | 99.76 | 99.81 | 99.62 |

As shown in Table I, the method of the invention affords ClPAMI in a conversion of at least 99.75% after 7 hours or less. By contrast, the control afforded ClPAMI at a lower conversion level after a much greater reaction time.

EXAMPLE 4

This example illustrates an imidization reaction run with an initial excess of one reactant. A 50 gallon glass-lined reactor was charged with o-dichlorobenzene (ODCB; 108.9 kilograms [Kg]), 4-chlorophthalic anhydride (ClPA) (9.990 Kg, 54.7217 moles) and m-phenylenediamine (2.9411 Kg, 27.2247 moles) to give a 0.50 mole % excess of ClPA based on 100% pure 4-ClPA. The ClPA contained from 0.5 to 1 mole % impurities. The reaction was slowly heated to about 180° C. over 4 hours and kept in this temperature range for 28 hours, during which time distillate was collected. Samples of the reaction slurry were obtained using a ¼ inch diameter glass tube at 4, 5, 6 and 21 hours after charging the reactor, and analyzed using High Performance Liquid Chromatography (HPLC). At 24 hours additional 4-ClPA (40 g, 0.219 moles) was added to consume residual monoamine that persisted in the reaction. A sample taken at 28 hrs showed that monoamine was consumed. The slurry was suitable for polymerization to polyetherimide.

EXAMPLE 5

The procedure of Example 4 was repeated except that the initial formulation was 2.5 mole % (based on moles of diamine) deficient in 4-ClPA. Also 0.25% (by weight based on the total of diamine and anhydride) of sodium phenylphosphinate catalyst was added to the formulation. After heating at reflux overnight the 2.5 mol % ClPA withheld was added to consume the residual monoamine. A sample taken 4 hours after this ClPA addition showed no detectable monoamine and high conversion to ClPAMI.

In the polyether polymer preparation method of the invention, the alkali metal salts of dihydroxy-substituted aromatic hydrocarbons (hereinafter sometimes simply "bisphenol salt" for brevity) which are employed are typically sodium and potassium salts. Sodium salts are frequently preferred by reason of their availability and relatively low cost. Said salt may be employed in anhydrous or hydrated form; the anhydrous form is usually preferred.

Suitable dihydroxy-substituted aromatic hydrocarbons include those having the formula

wherein $A^2$ is a divalent aromatic hydrocarbon radical. Suitable $A^2$ radicals include m-phenylene, p-phenylene, 4,4'-biphenylene, 4,4'-bi(3,5-dimethyl)phenylene, 2,2-bis(4-phenylene)propane, 2,2,2',2'-tetrahydro-3,3,3',3'-tetramethyl-1,1'-spirobi[1H-indene]-6,6'-diol, and similar radicals such as those which correspond to the dihydroxy-substituted aromatic hydrocarbons disclosed by name or formula (generic or specific) in U.S. Pat. No. 4,217,438.

The $A^2$ radical preferably has the formula

wherein each of $A^3$ and $A^4$ is a monocyclic divalent aromatic hydrocarbon radical and Y is a bridging hydrocarbon radical in which one or two atoms separate $A^3$ from $A^4$. The free valence bonds in formula IV are usually in the meta or para positions of $A^3$ and $A^4$ in relation to Y. Compounds in which $A^2$ has formula IV are bisphenols, and for the sake of brevity the term "bisphenol" is sometimes used herein to designate the dihydroxy-substituted aromatic hydrocarbons; it should be understood, however, that non-bisphenol compounds of this type may also be employed as appropriate.

In formula IV, the $A^3$ and $A^4$ values may be unsubstituted phenylene or substituted derivatives thereof, illustrative substituents (one or more) being alkyl, alkenyl, and halogen, particularly bromine. Unsubstituted phenylene radicals are preferred. Both $A^3$ and $A^4$ are preferably p-phenylene, although both may be o- or m-phenylene or one o- or m-phenylene and the other p-phenylene.

The bridging radical, Y, is one in which one or two atoms, preferably one, separate $A^3$ from $A^4$. Illustrative radicals of this type are —C=O, —O—, —S—, —SO—, —SO$_2$—, methylene, cyclohexylmethylene, 2-[2.2.1]-bicycloheptylmethylene, ethylene, isopropylidene, neopentylidene, cyclohexylidene, cyclopentadecylidene, cyclododecylidene, adamantylidene; gem-alkylene (alkylidene) radicals are preferred. Also included, however, are unsaturated radicals. For reasons of availability and particular suitability for the purposes of this invention, the preferred radical of formula III is the 2,2-bis(4-phenylene) propane radical, which is derived from bisphenol A and in which Y is isopropylidene and $A^3$ and $A^4$ are each p-phenylene.

Spiro(bis)indane bisphenols may also be employed. They include 2,2,2',2'-tetrahydro-3,3,3',3'-tetramethyl-1,1'-spirobi [1H-indene]-6,6'-diol and its substituted analogs.

The substituted aromatic compounds of formula I which are employed in the present invention contain an aromatic radical $A^1$ and an activating radical Z. The $A^1$ radical is normally a di- or polyvalent $C_{6-10}$ radical, preferably monocyclic and preferably free from electron-withdrawing substituents other than Z. Unsubstituted $C_6$ aromatic radicals are especially preferred.

The Z radical is usually an electron-withdrawing group, which may be di- or polyvalent to correspond with the valence of $A^1$. Examples of divalent radicals are carbonyl, carbonylbis(arylene), sulfone, bis(arylene) sulfone, benzo-1,2-diazine and azoxy. Thus, the moiety —$A^1$—Z—$A^1$— may be a bis(arylene) sulfone, bis(arylene) ketone, tris(arylene)bis(sulfone), tris(arylene)bis(ketone), bis(arylene) benzo-1,2-diazine or bis(arylene)azoxy radical and especially one in which $A^1$ is p-phenylene.

Also included are compounds in which —$A^1$—Z—$A^1$— is a bisimide radical, illustrated by those of the formula

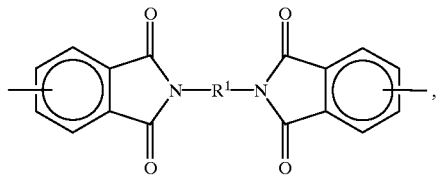

(V)

wherein $R^1$ is a $C_{6-20}$ divalent aromatic hydrocarbon or halogenated hydrocarbon radical, a $C_{2-20}$ alkylene or cycloalkylene radical, a $C_{2-8}$ bis(alkylene-terminated) polydiorganosiloxane radical or a divalent radical of the formula

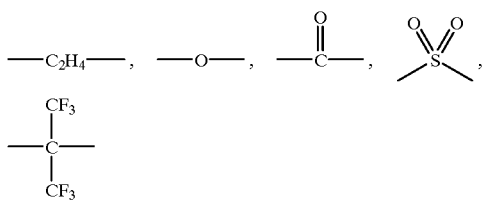

(VI)

in which Q is

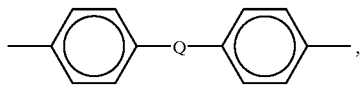

or a covalent bond. Most often, $R^1$ is at least one of m-phenylene, p-phenylene, 4,4'-oxybis(phenylene) and

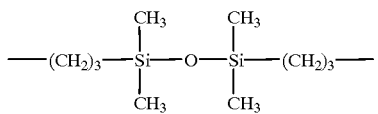

(VII)

Polyvalent Z radicals include those which, with $A^1$, form part of a fused ring system such as benzimidazole, benzoxazole, quinoxaline or benzofuran.

Also present in the substituted aromatic compound of formula I are two displaceable $X^1$ radicals which may be fluoro, chloro, bromo or nitro. In most instances, fluoro and chloro atoms are preferred by reason of the relative availability and effectiveness of the compounds containing them. The particularly preferred compound of formula I, for the purposes of the present invention, is ClPAMI.

Organic liquids employed in the polyether polymer preparation method of the invention are, in general, the same ones employed in the bis(halophthalimide) method. The substituted aromatic compound, most often a bis(halophthalimide), is supplied in the form of a slurry in said liquid. The bisphenol salt may be supplied by any convenient means, such as a slurry or a solid; a slurry is usually preferred.

Also present in the reaction mixture is a phase transfer catalyst, preferably one which is substantially stable at the temperatures employed; i.e., in the range of about 125–250° C. Various types of phase transfer catalysts may be employed for this purpose. They include quaternary phosphonium salts of the type disclosed in U.S. Pat. No. 4,273,712, N-alkyl-4-dialkylaminopyridinium salts of the type disclosed in U.S. Pat. Nos. 4,460,778 and 4,595,760, and guanidinium salts of the type disclosed in the aforementioned U.S. Pat. No. 5,229,482. Said patents and application are incorporated by reference herein. The preferred phase transfer catalysts, by reason of their exceptional stability at high temperatures and their effectiveness to produce high molecular weight aromatic polyether polymers in high yield are the hexaalkylguanidinium and α,ω-bis(pentaalkylguanidinium)alkane salts.

The bisphenol salt and substituted aromatic compound are typically brought into contact in substantially equimolar amounts. For maximum molecular weight, the amounts should be as close as possible to exactly equimolar, but molecular weight control may be achieved by employing one reagent or the other in slight excess. It is also within the scope of the invention to employ monofunctional reagents such as monohydroxyaromatic compounds or monohalo- or nitroaromatic compounds as chain termination agents. The monohalo- or nitroaromatic compounds may, as previously noted, be prepared, for example, by the reaction of diamino compounds with halophthalic anhydrides containing unsubstituted phthalic anhydride as an impurity.

Reaction temperatures are in the range of about 125–250° C., preferably about 130–225° C. The proportion of phase transfer catalyst is generally about 0.5–10 and preferably about 1–5 mole percent based on bisphenol salt. For best results, an intimate mixing method such as vigorous stirring is employed since the rate of the polymerization reaction is typically dependent on efficiency of mixing.

Following completion of the reaction, the aromatic polyether polymer may be isolated by conventional methods. This typically includes such steps as acid quenching or neutralization followed by washing, evaporation of solvent, or anti-solvent precipitation and/or devolatilization-pelletization.

The polyether polymer preparation method of the invention is illustrated by the following examples. All percentages are by weight. The ClPAMI employed was prepared from two sources of 4-chlorophthalic anhydride. Sample A was prepared from distilled anhydride; it contained 0.3% phthalic acid and, upon exposure to moisture, was partially hydrolyzed to a content of 4.6% of the corresponding chlorophthalic acid. During the ClPAMI formation reaction, phthalic acid was converted to m-ClPAMI which served as a chain termination agent. Sample B was prepared from anhydride produced by palladium-catalyzed decarbonylation of trimellitic anhydride acid chloride and contained no phthalic acid. The amount of bisphenol A disodium salt employed in each example was an amount calculated as 1.5 mole % in excess with respect to pure ClPAMI.

EXAMPLES 6–10

Each example employed a ClPAMI product (sample A or B) in the form of a paste prepared according to Example 2. It was dried by addition of 12 successive 50-ml portions of dry (maximum 5 ppm water) anisole and distillation under a positive argon atmosphere, and finally reduced again to a paste containing about 10 ml of anisole.

A 250 ml three-necked round-bottomed flask, fitted with a stirrer and male joint, was charged with bisphenol A disodium salt and 100 ml of dry anisole. The mixture was dried by distillation under a positive argon atmosphere with removal of about 65 ml of anisole. It was then quantitatively transferred under argon pressure through an oven-dried adapter into the ClPAMI slurry. The combined mixture was heated in an oil bath at 170° C., and 3.5 mole percent (based on bisphenol A salt) of hexaethylguanidinium chloride dissolved in anisole was added, also under argon. The mixture was heated under reflux for 4 hours to yield the desired polyetherimide. In each example the weight average molecular weight was determined by gel permeation chromatography; to avoid variations in analysis, it was additionally expressed as "Mw ratio" which is a percentage of the molecular weight of a single sample of commercial polyetherimide whose molecular weight was determined at the same time. The commercial polyetherimide was prepared by a method similar to that described in U.S. Pat. No. 3,838,097.

The results are given in Table II, in comparison with a control in which a solid isolated ClPAMI reagent was employed.

TABLE 11

| Example | 6 | 7 | 8 | 9 | 10 | Control |
|---|---|---|---|---|---|---|
| ClPAMI sample | A | A | A | B | B | Solid |
| Slurry analysis: | | | | | | |
| Amic acids, % | 0.25 | 0.28 | 0.19 | 0.21 | 0.24 | <0.1 |
| m-ClPAMI, % | 0.363 | 0.242 | 0.200 | 0 | 0.68* | 0 |
| Polyetherimide Mw | 70,900 | 68,800 | 75,600 | 85,800 | 81,200 | 87,000 |
| Mw ratio, % | 127 | 126.7 | 135 | 153.7 | 150 | 155.7 |

*Pure m-ClPAMI added before polymerization.

It can be seen that the polyetherimide preparation method of the invention affords polymers having molecular weights comparable to or approaching that of a product prepared from solid ClPAMI. It is also apparent that amic acid proportions above 0.25%, as illustrated by Example 7, cause a decrease in molecular weight.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention.

What is claimed is:

1. A method for preparing a bis(halophthalimide) in organic slurry form which comprises effecting contact at a temperature of at least 100° C. between the constituents of a mixture comprising at least one diamino compound, at least one halophthalic anhydride, an organic liquid having a polarity no higher than that of o-dichlorobenzene, dichlorotoluene, 1,2,4-trichlorobenzene, diphenyl sulfone and anisole; and an imidization catalyst, said mixture having a solids content of at least about 5% by weight, thereby producing a slurry of said bis(halophthalimide) in said liquid.

2. The method according to claim 1 wherein the diamino compound is at least one aromatic diamine.

3. The method according to claim 2 wherein the solids content is at least about 12% by weight.

4. The method according to claim 3 wherein the temperature is at least 150° C.

5. The method according to claim 4 wherein the molar ratio of anhydride to diamine is 2:1 or is adjusted to that value.

6. The method according to claim 1 wherein the organic liquid is o-dichlorobenzene or anisole.

7. The method according to claim 4 wherein the aromatic diamine is m- or p-phenylenediamine or a mixture thereof.

8. The method according to claim 4 wherein the halophthalic anhydride is at least one of 4-chlorophthalic anhydride, 3-chlorophthalic anhydride, 4-fluorophthalic anhydride, or 3-fluorophthalic anhydride.

9. The method according to claim 4 wherein the temperature is in the range of about 175–225° C.

10. The method according to claim 4 wherein the imidization catalyst is a salt of an organophosphorus acid or a heterocyclic amine.

11. The method according to claim 10 wherein the imidization catalyst is sodium phenylphosphinate.

12. The method according to claim 4 wherein the solids content is in the range of about 15–25%.

13. The method according to claim 12 wherein a mixture of water and organic liquid distilling from a reactor is sent to a distillation column where water is taken off overhead and solvent is recycled back into the reactor at a rate to maintain or increase the solids content.

14. The method according to claim 1 wherein the reaction is performed under super-atmospheric pressure.

15. A method for preparing 1,3-bis[N-(4-chlorophthalimido)]benzene in organic slurry form which comprises effecting contact at a temperature in the range of about 175–225° C. between the constituents of a mixture comprising at least m-phenylenediamine or a mixture thereof with p-phenylenediamine, 4-chlorophthalic anhydride, an imidization catalyst and o-dichlorobenzene or anisole, said mixture having a solids content in the range of about 15–25% by weight, thereby producing a slurry of said bis(halophthalimide) in said o-dichlorobenzene or anisole.

16. A method for preparing an aromatic polyether polymer which comprises contacting, in at least one organic liquid as diluent, substantially equimolar amounts of at least one alkali metal salt of a dihydroxy-substituted aromatic hydrocarbon and a slurry in said organic liquid of at least one substituted aromatic compound of the formula $$Z(A^1\text{—}X^1)_2, \qquad (I)$$

wherein Z is an activating radical, $A^1$ is an aromatic radical and $X^1$ is fluoro, chloro, bromo or nitro, in the presence of a catalytically active amount of a phase transfer catalyst, wherein said slurry of at least one substituted aromatic compound comprises the reaction product of a mixture comprising at least one diamino compound, at least one halophthalic anhydride, an organic liquid and an imidization catalyst, said mixture having a solids content of at least about 5% by weight, and wherein any of the organic liquids has a polarity no higher than that of o-dichlorobenzene, dichlorotoluene, 1,2,4-trichlorobenzene, diphenyl sulfone and anisole.

17. The method according to claim 16 wherein the organic liquid is o-dichlorobenzene or anisole.

18. The method according to claim 16 wherein the phase transfer catalyst is a quaternary phosphonium salt, an alkylaminopyridinium salt or a guanidinium salt.

19. The method according to claim 18 wherein the phase transfer catalyst is a hexaalkylguanidinium or an α,ω-bis(pentaalkylguanidinium)alkane salt.

20. The method according to claim 16 wherein the dihydroxy-substituted aromatic hydrocarbon has the formula HO—$A^3$—Y—$A^4$—OH, wherein each of $A^3$ and $A^4$ is a monocyclic divalent aromatic hydrocarbon radical and Y is a bridging hydrocarbon radical in which one or two atoms separate $A^3$ from $A^4$.

21. The method according to claim 16 wherein $A^1$ is p-phenylene.

22. The method according to claim 16 wherein —$A^1$—Z—$A^1$— is a bisimide radical of the formula

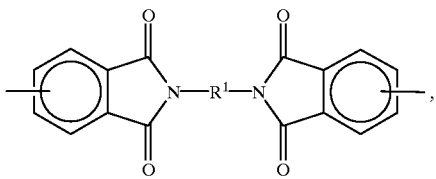

(V)

wherein $R^1$ is a $C_{6-20}$ divalent aromatic hydrocarbon or halogenated hydrocarbon radical, a $C_{2-20}$ alkylene or cycloalkylene radical, a $C_{2-8}$ bis(alkylene-terminated) polydiorganosiloxane radical or a divalent radical of the formula

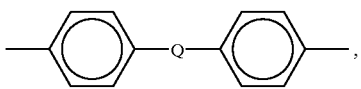

(VI)

in which Q is

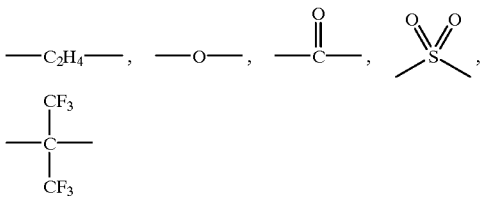

or a covalent bond.

23. The method according to claim 22 wherein said substituted aromatic compound contains no more than 0.25% by weight of amic acids.

24. The method according to claim 23 wherein $R^1$ is m-phenylene or a mixture thereof with p-phenylene.

25. The method according to claim 21 wherein $X^1$ is chloro or fluoro.

26. The method according to claim 16 wherein the dihydroxy-substituted aromatic hydrocarbon is bisphenol A.

27. The method according to claim 16 wherein the reaction temperature is in the range of about 130–225° C.

28. The method according to claim 16 wherein the phase transfer catalyst is a guanidinium salt.

29. The method according to claim 28 wherein the proportion of phase transfer catalyst employed is about 1–5 mole percent based on the dihydroxy-substituted aromatic hydrocarbon salt.

30. A method for preparing a polyetherimide which comprises contacting, in o-dichlorobenzene or anisole as diluent, substantially equimolar amounts of bisphenol A disodium salt and a slurry in said o-dichlorobenzene or anisole of 1,3-bis[N-(4-chlorophthalimido)]benzene, in the presence of a catalytically active amount of a hexaalkylguanidinium chloride as a phase transfer catalyst; wherein said slurry of 1,3-bis[N-(4-chlorophthalimido)]benzene comprises the reaction product of a mixture comprising m-phenylenediamine; 4-chlorophthalic anhydride; and o-dichlorobenzene or anisole; and an imidization catalyst, said mixture having a solids content of at least about 5% by weight.

31. The method according to claim 8 wherein the halophthalic anhydride is 4-chlorophthalic anhydride.

32. The method according to claim 16 wherein Z is a carbonyl radical.

33. The method according to claim 16 wherein the solids content is at least about 12% by weight.

34. The method according to claim 30 wherein the solids content is at least about 12% by weight.

35. The method according to claim 30 wherein the 1,3-bis[N-(4-chlorophthalimido)]benzene contains no more than 0.25% by weight of amic acids.

* * * * *